United States Patent [19]
Jarrett et al.

[11] Patent Number: 4,788,979
[45] Date of Patent: Dec. 6, 1988

[54] BIOABSORBABLE COATING FOR A SURGICAL ARTICLE

[75] Inventors: Peter K. Jarrett, Trumbull; Donald J. Casey, Ridgefield; Leonard T. Lehmann, Danbury, all of Conn.

[73] Assignee: American Cyanamid Company, Stamford, Conn.

[21] Appl. No.: 172,608

[22] Filed: Mar. 24, 1988

Related U.S. Application Data

[63] Continuation-in-part of Ser. No. 910,598, Sep. 23, 1986, abandoned.

[51] Int. Cl.⁴ .............................................. A61L 17/00
[52] U.S. Cl. ................................. 128/335.5; 528/354; 528/361; 428/395
[58] Field of Search ...................... 528/354, 359, 361; 428/395; 128/335.5

[56] References Cited

U.S. PATENT DOCUMENTS

| 3,982,543 | 9/1976 | Schmitt et al. | 427/2 X |
| 4,027,676 | 6/1977 | Mattei | 427/2 X |
| 4,048,256 | 9/1977 | Casey et al. | 525/444 |
| 4,057,537 | 11/1977 | Sinclair | 528/354 |
| 4,201,216 | 5/1980 | Mattei | 128/335.5 |
| 4,595,713 | 6/1986 | St. John | 528/354 X |
| 4,605,730 | 8/1986 | Shalaby et al. | 528/354 X |
| 4,624,256 | 11/1986 | Messier et al. | 128/335.5 |

Primary Examiner—Earl Nielsen
Attorney, Agent, or Firm—Charles F. Costello, Jr.

[57] ABSTRACT

A bioabsorbable coating for a surgical article comprises a copolymer manufactured from the monomer caprolactone and at least one other copolymerizable monomer. The surgical article can be a bioabsorbable suture or ligature.

26 Claims, No Drawings

BIOABSORBABLE COATING FOR A SURGICAL ARTICLE

CROSS-REFERENCE TO RELATED APPLICATION

This is a continuation-in-part application of U.S. Ser. No. 910,598 filed Sept. 23, 1986, now abondoned.

BACKGROUND AND SUMMARY OF THE INVENTION

A bioabsorbable coating for a surgical article comprises a copolymer manufactured from the monomer caprolactone and at least one other copolymerizable monomer. The surgical article can be a bioabsorbable suture or a ligature. A surgical suture or ligature coated with the bioabsorbable copolymer of this invention has improved knot repositioning properties.

The bioabsorbable coating of this invention has advantages over prior art coatings used with surgical stutures or ligatures. Specifically, sutures coated with the copolymer coating of this invention are less stiff than sutures using the coatings described in the prior art; see examples 6 and 10 in U.S. Pat. Nos. 3,867,190 and 3,736,646 which are incorporated herein by reference. Also, the processes for coating a bioabsorbable surgical article are not clearly described in the prior art. That is, the process of this invention uses a copolymer manufactured from at least about 50 percent by weight of the monomer caprolactone and the remainder glycolide. Copolymers of these proportions are soluble in acetone, as contrasted with, for example, the copolymers of lactide and glycolide discussed in U.S. Pat. No. 4,201,216, which is incorporated herein by reference.

The use of a copolymer of caprolactone and glycolide as a suture is known in the prior art, for example, as disclosed in U.S. Pat. Nos. 4,700,704 (e.g. claim 1) and 4,605,730 (examples I to XI), and in example 5 of U.S. Pat. Nos. 4,300,565 and 4,243,775. All of these patents are incorporated herein by reference.

The use of a copolymer of at least 90% by weight caprolactone and another biodegradable monomer, e.g. glycolide, as a coating is disclosed in U.S. Pat. No. 4,624,256. See also U.S. Pat. Nos. 4,190,720 (column 1) and 3,942,532 (example II), which are disclosed in the '256 patent. These two latter patents disclose a copolymer ('720) or homopolymer ('532) of $\epsilon$-caprolactone. In the '720 patent, the copolymer is disclosed as a film; in the '532 patent the homopolymer is dislcosed as a suture coating. It is not seen in either of the latter two patents where the respective polymers are disclosed as bioabsorbable. All of these patents are incorporated herein by reference.

The bioabsorbable coating of this invention has superior and unexpected results over the known commercially available surgical suture or ligature coatings. For example, the coating of this invention does not present a hazy appearance on a suture. The coating can be dissolved in acetone which seems to be less deleterious than other known solvents, for example, methylene chloride. Further, suture characteristics such as knot-snug-in or repositioning, and tissue drag appear to be equal to, if not better than suture coatings disclosed in the prior art.

A bioabsorbable coating for a surgical article comprising a block copolymer has been invented. The block copolymer has one or more blocks manufactured from the monomer caprolactone.

The term block copolymer described in this invention means a copolymer with a non-random distribution of comonomer units along the chain. A convenient shorthand notation to describe different block architectures utilizes alphabetic symbols for the individual block segments. The number and types of comonomer units within a block segment can be specified. For example, AB represents a diblock copolymer, ABA or BAB represents a triblock copolymer. More complex architectures such as tetrablocks or pentablocks, etc., can also be described using this notation, e.g., ABABA. A multiblock copolymer can be represented as $-AB-_n$. If more than two types of blocks are present, additional alphabetic symbols can be defined.

Block copolymers are formed in this ivnention by the sequential addition of comonomers or mixtures of comonomers to a reactor. It is believed that with this type of preparation method, there can be a distribution of block size and block composition and that the chain architecture can be compromised by ester interchange reactions.

The term random or randomly in this invention means the result of a copolymerization reaction in which all of the monomers are charged into a reactor simultaneously. It is to be understood that variations in reaction conditions can lead to some differences in the actual degree of randomness with respect to the distribution of comonomer units in a copolymer chain.

In one embodiment, the caprolactone is $\epsilon$-caprolactone. In another embodiment the copolymer is a diblock copolymer.

In a preferred embodiment, the copolymer has one or more A blocks solely manufactured from the monomer caprolactone, and one or more B blocks manufactured from one or more monomers selected from the group consisting of lactides, carbonates, lactones and oxalates, with the proviso that in the latter one or more B blocks, caprolactone can only be used with another monomer. In a further embodiment, the inherent viscosity of the block copolymer is about 0.1 to 1.0 dl/g (0.5 g/dl in CHCl$_3$, 30° C.), the melting point of the block copolymer is less than 70° C., and the block copolymer is soluble in acetone or methylene chloride.

In a specific embodiment, the coating comprises a block copolymer consisting of one or more A blocks of formula (I):

and the remaining one or more B blocks comprising one or more of the formulas (II) to (VI), either alone or in combination with formula (I):

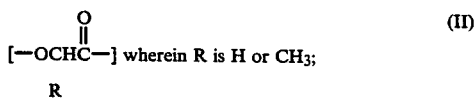

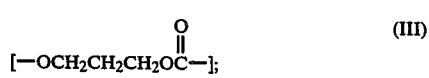

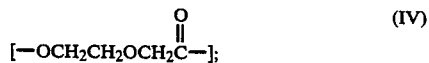

-continued $$[-OCHCHR'CH_2C(=O)-] \text{ wherein } R' \text{ is } CH_3 \text{ or } C_2H_5; \quad (V)$$

$$[-O(CH_2)_4C(=O)-], \quad (VI)$$

the total amount of formula (I) in the copolymer being more than 50 to about 80 percent by weight of said copolymer.

In one embodiment, the remaining one or more B blocks consist of formulas (I) and (II). In another embodiment the remaining one or more B blocks consist of formulas (II) and (III).

In a specific embodiment, the formula (II) is:

$$[-O-CH_2-C(=O)-].$$

The surgical article coated with the above-described polymers can be bioabsorbable. In one embodiment, the bioabsorbable surgical article is a suture or ligature. In a specific embodiment, the suture or ligature is manufactured from a polymer prepared from one or more monomers selected from the group consisting of lactides, carbonates and lactones. If the polymer in the suture or ligature and the copolymer in the coating are prepared from the same monomers, it is to be understood that the copolymer in the coating has a melting point less than about 70° C. and is soluble in acetone or methylene chloride. It is to be further understood that this description applies by implication to the description of the invention in the claims.

In a more specific embodiment, the suture or ligature is manufactured from a homopolymer prepared from the monomer glycolide. In another specific embodiment, the suture or ligature is manufactured from a polymer prepared from at least the monomer lactide. In yet another more specific embodiment, the suture or ligature is manufactured from a copolymer prepared from the monomers glycolide and 1,3-dioxan-2-one. In a further specific embodiment, the suture or ligature is manufactured from a copolymer prepared from the monomers glycolide and lactide.

The suture or ligature can be in multifilamentary form. In a specific embodiment, the coating comprises about 1/10 to 5% by weight of the coated multifilamentary suture or ligature. In a more specific embodiment, the coating comprises about ¼ to 3% by weight of the coated multifilamentary suture or ligature. In the more specific embodiment, the coating can comprise up to about 2 ½ percent by weight of the coated multifilamentary suture or ligature.

A coating process for a bioabsorbable surgical article comprises dissolving in acetone a block copolymer having one or more A blocks manufactured solely from the monomer caprolactone and one or more B blocks manufactured from the monomers caprolactone and glycolide, where the glycolide in the one or more B blocks comprises up to 50 percent by weight of the copolymer and up to about 65 percent by weight of said B blocks; contacting the surgical article with the dissolved copolymer; maintaining the contact between the surgical article and the dissolved copolymer until the copolymer on the article comprises from about 1/10 to 5% by weight of the coated surgical article; removing the coated surgical article from the dissolved copolymer; and drying the copolymer coating on the surgical article.

In one embodiment, the caprolactone is ε-caprolactone.

DESCRIPTION OF THE PREFERRED EMBODIMENT(S)

The following examples describe the best mode of making and using the coatings of this invention. Unless otherwise specified, all of the inherent viscosity ($\eta$inh) measurements in the examples were conducted at 30° C. Inherent viscosities are expressed in units of deciliters per gram (dl/g). The solution concentrations used to measure $\eta$inh are expressed in units of grams of polymer per deciliter of solution and are set in parentheses following the $\eta$inh value. The solvents used were either chloroform ($CHCl_3$) or hexafluoroacetone sesquihydrate (HFAS).

A description of inherent viscosity using the nomenclature described above is disclosed in the prior art, e.g. in Kinematic Glass Viscometers, ASTM D2515; Dilute Solution Viscosities of Polymers, ASTM D2857; Dilute Solution Viscosity of Ethylene Polymers, ASTM D1601; Techniques of Polymer Characterization; P. Allen, Ed., Butterworth Scientific Publications, London, 1959, chapter 6; Kirk-Othmer Encyclopedia of Chemical Technology, Second Ed., John Wiley & Sons, 1968, vol 16, pages 242-253; and Polymer Handbook, J. Brandrup & E. Immergut, Ed., Interscience, NY, pages IV-1 to IV-2. All of this prior art is incorporated herein by reference.

It is to be understood that an increase in the inherent viscosity of the copolymer will provide for an increase in the knot security but also an increase in the absorption time of the coated surgical article and in the work required to reposition a knot.

The term block copolymer described in this invention means a copolymer with a non-random distribution of comonomer units along the chain. A convenient shorthand notation to describe different block architecture utilizes alphabetic symbols for the individual block segments. The number and types of comonomer units within a block segment can be specified. For example, AB represents a diblock copolymer, ABA or BAB represents a triblock copolymer. More complex architectures such as tetrablocks or pentablocks, etc., can also be described using this notation, e.g. ABABA. A multiblock copolymer can be represented as —AB—$_n$. If more than two types of blocks are present, additional alphabetic symbols can be defined.

Block copolymers are formed in this invention by the sequential addition of comonomers or mixtures of comonomers to a reactor. It is believed that with this type of preparation method, there can be a distribution of block size and block composition and that the chain architecture can be comprised by ester interchange reactions.

The term random or randomly in this invention means the result of a copolymerization reaction in which all of the monomers are charged into a reactor simultaneously. It is to be understood that variations in reaction conditions can lead to some differences in the actual egree of randomness with respect to the distribution of comonomer units in a copolymer chain.

EXAMPLE 1

Synthesis of ε-Caprolactone-(ε-Caprolactone-Glycolide) AB Block Copolymer

ε-Caprolactone (80g, 0.70 mole), lauryl alcohol (1.585 ml, $6.6 \times 10^{-3}$ mole) and stannous octoate (39.5 ul, $1.22 \times 10^{-4}$ mole) were combined in a stirred reactor at 180° C. The mixture was stirred while the temperature was increased to 200° C. over 8 min. and stirring was continued for 1.5 hours. Glycolide (60g, 0.52 mole) and ε-Caprolactone (60 g, 0.53 mole) were added and the temperature was reduced to 180° C. Stirring was maintained for 2 hours longer. The copolymer was discharged from the reactor and was dried in a vacuum oven for 24 hours at about 50° C. to remove residual monomer. The analyzed properties of the resulting copolymer are listed in Table I, Section A.

EXAMPLES 2-14

Synthesis of ε-Caprolactone-(ε-Caprolactone-Glycolide) AB Block Copolymers

A series of ε-caprolactone-glycolide copolymers was prepared by the general procedure described in Example 1, although the polymerization temperature was maintained at about 180° C. throughout the reaction in these examples. Specific preparative details and properties of the resulting copolymers are summarized in Table I, Section A.

EXAMPLES 15-18

Synthesis of ε-Caprolactone-(Glycolide—1,3-Dioxan—2-one) AB Block Copolymers A series of copolymers containing ε-caprolactone, glycolide and 1,3-dioxan—2-one were prepared by the same general procedure described in Example 1, with the exception that the second charge contained glycolide and 1,3-dioxan—2-one. The temperature was held at about 180° C. throughout the reaction in each of these examples. Specific preparative details and properties of the resulting copolymers are summarized in Table I, Section B.

TABLE I

Section A
Caprolactone/Glycolide Copolymer Properties

| | Polymerization Conditions | | | | | | | NMR[4] | | | DSC[5] | | $\eta inh$[6] | Solubility in |
|---|---|---|---|---|---|---|---|---|---|---|---|---|---|---|
| | 1st Charge | | 2nd Charge | | | Mole % | | Wt % | | | Tm | Δ H | | |
| Example | Cap[1] | Time(hrs) | Cap[1] | Gly[1] | Time(hrs) | LA[2] | T-9[3] | Cap | $\overline{L_c}$ | $\overline{L_g}$ | °C. | Cal/g | CHCl$_3$ | Acetone |
| 1 | 40 | 1.5 | 30 | 30 | 2.0 | 0.40 | .007 | 69.6 | 2.98 | 2.78 | 58 | 10.1 | 0.54 | Gels > 4% |
| 2 | 40 | 1.5 | 30 | 30 | 3.0 | 1.53 | .01 | 70.1 | 2.62 | 2.20 | 56 | 8.5 | 0.27 | Sol. |
| 3 | 40 | 1.5 | 30 | 30 | 3.0 | 2.29 | .01 | 70.6 | 2.46 | 2.22 | 54 | 7.9 | 0.22 | Sol. |
| 4 | 40 | 1.5 | 30 | 30 | 3.0 | 4.65 | .01 | 73.2 | 2.57 | 2.08 | 47 | 8.2 | 0.13 | Sol. |
| 5 | 30 | 1.5 | 42 | 28 | 2.5 | 1.15 | .01 | 72.0 | 2.22 | 1.75 | 55 | 6.2 | 0.34 | Sol. |
| 6 | 30 | 1.5 | 42 | 28 | 2.0 | 1.72 | .01 | 71.9 | 2.14 | 1.73 | 42 | 5.4 | 0.27 | Sol. |
| 7 | 20 | 1.5 | 40 | 40 | 2.0 | 0.40 | .01 | 57.9 | 1.85 | 2.75 | 54 | 6.7 | 0.51 | Sol/Hazy |
| 8 | 20 | 1.5 | 48 | 32 | 3.0 | 0.40 | .01 | 64.4 | 1.94 | 2.23 | 58 | 5.0 | 0.46 | Sol. |
| 9 | 20 | 1.5 | 48 | 32 | 3.0 | 1.15 | .007 | 68.0 | 1.80 | 1.77 | 50 | 3.7 | 0.33 | Sol. |
| 10 | 20 | 1.5 | 48 | 32 | 3.0 | 0.77 | .01 | 67.0 | 1.82 | 1.84 | 55 | 4.1 | 0.39 | Sol. |
| 11 | 20 | 1.5 | 52 | 28 | 2.0 | 0.40 | .01 | 71.6 | 1.99 | 1.57 | 56 | 5.4 | 0.59 | Sol. |
| 12 | 10.5 | 1.5 | 58.2 | 31.3 | 3.0 | 0.40 | .007 | 66.0 | 1.66 | 1.71 | 56 | 2.4 | 0.55 | Sol. |
| 13 | 10.5 | 1.5 | 53.7 | 35.8 | 3.0 | 0.40 | .007 | 61.3 | 1.55 | 2.04 | 55 | 2.4 | 0.33 | Sol. |
| 14 | 3.5 | 1.5 | 62.7 | 33.8 | 2.5 | 0.40 | .007 | 63.3 | 1.50 | 1.71 | 42 | 0.5 | 0.55 | Sol. |

[1] Numbers under these categories represent the Wt % of the added monomer with respect to the weight of the total copolymer.
[2] Lauryl Alcohol as initiator.
[3] Stannous Octoate catalyst purchased from M&T Chemicals.
[4] Nuclear Magnetic Resonance Spectrometry. $L_c$ is the average segment length of consecutive caprolactone units in the polymer. $L_g$ is the average segment length of glycolide units.
[5] Differential scanning calorimetry. Tm is the melting temperature (peak), Δ H is the heat of fusion.
[6] Inherent viscosity of a 0.5 g/dl solution of polymer in chloroform.

Section B
Caprolactone/Glycolide/1,3-Dioxan-2-one Copolymer Properties

| | Charged Composition | | | | | | | NMR[4] | | | DSC[5] | | $\eta inh$[6] | Solubility in |
|---|---|---|---|---|---|---|---|---|---|---|---|---|---|---|
| | 1st Charge | | 2nd Charge | | | Mole % | | Wt % | | | Tm | Δ H | | |
| Example | Cap[1] | Time(hrs) | GLY[1] | TMC[1] | Time (hrs) | LA[2] | T-9[3] | Cap | Gly | TMC | °C. | Cal/g | CHCl$_3$ | CH$_2$Cl$_2$ |
| 15 | 20 | 1.5 | 40 | 40 | 2.0 | 0.40 | .01 | 18.9 | 41.6 | 39.5 | 51 | 2.8 | 0.39 | Sol. |
| 16 | 20 | 1.5 | 40 | 40 | 3.0 | 0.73 | .01 | 18.8 | 41.6 | 39.6 | 48 | 3.1 | 0.29 | Sol. |
| 17 | 20 | 1.5 | 40 | 40 | 3.0 | 1.10 | .01 | 17.5 | 41.5 | 41.0 | 49 | 3.0 | 0.26 | Sol. |
| 18 | 40 | 1.5 | 30 | 30 | 3.0 | 1.48 | .01 | 37.4 | 30.8 | 31.8 | 57 | 8.2 | 0.23 | Sol. |

[1] Numbers under these categories represent the Wt % of the added monomer with respect to the weight of the total copolymer. TMC is an abbreviation for trimethylene carbonate which is the same as 1,3 dioxan-2-one.
[2] Lauryl Alcohol as initiator.
[3] Stannous Octoate catalyst purchased from M&T Chemicals.
[4] Nuclear Magnetic Resonance Spectrometry.
[5] Differential scanning calorimetry. Tm is melting temperature (peak), Δ H is the heat of fusion.
[6] Inherent viscosity of a 0.5 g/dl solution of polymer in chloroform.

Table II summarizes the in vitro performance for the bioabsorbable coatings of this invention.

TABLE II

Section A
In Vitro Coating Performance of
Cap/Gly AB Copolymers

TABLE II-continued

| | | 15 mm SNUG-IN[2] | | 10 mm SECURITY[3] | | Hand Tested[4] |
|---|---|---|---|---|---|---|
| Example | Wt. %[1] Coating | WORK (Kg mm) | S. DEV. | WORK (Kg mm) | S. DEV. | Wet Knot Run Down |
| 1 | 0.75 | 3.31 | 1.93 | 18.96 | 2.28 | R |
| | 1.38 | 8.04 | 2.28 | 21.49 | 1.24 | R |
| | 1.91 | 17.80 | 4.61 | 21.68 | 1.72 | RW |
| 2 | 0.76 | 1.86 | 1.37 | 12.94 | 4.03 | RW |
| | 1.39 | 1.07 | 0.33 | 15.49 | 1.19 | R |
| | 2.24 | 3.02 | 0.75 | 17.52 | 1.77 | RW |
| 3 | 0.88 | 1.52 | 0.86 | 15.09 | 3.03 | R |
| | 1.37 | 4.00 | 3.16 | 14.94 | 2.12 | R |
| | 2.04 | 7.82 | 2.37 | 15.30 | 3.60 | RW |
| 4 | 0.55 | 1.58 | 0.50 | 15.32 | 2.55 | R |
| | 1.77 | 8.56 | 6.71 | 15.98 | 2.75 | R |
| | 1.91 | 5.99 | 2.91 | 17.63 | 0.94 | R |
| 5 | 0.80 | 3.37 | 4.96 | 11.61 | 4.23 | RW |
| | 1.44 | 3.12 | 2.21 | 12.29 | 2.89 | RW |
| | 2.00 | 1.87 | 0.60 | 12.25 | 3.81 | RW |
| 6 | 0.89 | 0.76 | 0.23 | 11.41 | 4.85 | R |
| | 1.34 | 1.08 | 0.19 | 12.61 | 3.83 | RW |
| | 1.93 | 2.26 | 2.23 | 15.08 | 2.02 | RW |
| 7 | 0.66 | 13.99 | 5.76 | 19.47 | 1.97 | RC |
| | 1.31 | 20.97 | 2.16 | 20.60 | 2.05 | RC/RD |
| | 1.95 | 22.53 | 4.78 | 21.07 | 1.77 | RC/RD |
| 8 | 0.70 | 9.17 | 3.70 | 15.24 | 1.83 | RC |
| | 1.25 | 7.56 | 2.53 | 14.57 | 2.19 | R |
| | 1.78 | 15.79 | 7.04 | 15.57 | 2.75 | RW |
| 9 | 0.75 | 0.85 | 0.29 | 11.78 | 1.99 | RW |
| | 1.38 | 1.46 | 0.31 | 11.61 | 2.95 | RW |
| | 1.83 | 3.10 | 3.12 | 11.78 | 2.79 | RW |
| 10 | 0.66 | 2.07 | 1.19 | 10.62 | 3.40 | R |
| | 1.38 | 3.96 | 1.35 | 13.29 | 1.95 | R |
| | 2.10 | 5.98 | 3.61 | 10.98 | 3.33 | RW |
| 11 | 0.72 | 1.91 | 0.62 | 13.64 | 3.76 | RW |
| | 1.41 | 8.03 | 2.82 | 13.59 | 3.50 | RW |
| | 2.06 | 10.22 | 2.07 | 13.69 | 3.35 | RW |
| 12 | 0.61 | 7.79 | 5.53 | 14.06 | 3.21 | R |
| | 1.35 | 7.44 | 4.84 | 14.95 | 3.81 | R |
| | 1.94 | 9.17 | 1.47 | 16.02 | 1.88 | RW |
| 13 | 0.75 | 10.31 | 8.07 | 16.18 | 1.74 | R |
| | 1.38 | 16.66 | 3.76 | 16.49 | 1.56 | RW |
| | 1.95 | 14.39 | 1.28 | 17.44 | 2.01 | R |
| 14 | 0.78 | 13.36 | 3.04 | 16.58 | 2.90 | RC |
| | 1.50 | 16.46 | 11.46 | 14.81 | 2.46 | R |
| | 2.24 | 12.45 | 3.10 | 16.67 | 1.40 | RW |
| Uncoated Braid | — | 38.32 | 5.29 | 17.95 | 4.44 | L |

Section B
In Vitro Coating Performance
of Cap/Gly/1.3-Dioxan-2-one AB Copolymers

| Example | # Dips[1] | Hand Tested Wet Knot Run Down[4] |
|---|---|---|
| 15 | 1 | R |
| | 2 | R |
| | 3 | R |
| 16 | 1 | R |
| | 2 | R |
| | 3 | R |
| 17 | 1 | R |
| | 2 | R |
| | 3 | R |
| 18 | 1 | R |
| | 2 | R |
| | 3 | R |

TABLE II FOOTNOTES
[1]The coatings were applied to 1/0 polyglycolic acid braid from a 3.5% (wt/vol.) solution of the coating material dissolved in acetone using a capillary coating machine (all Section A copolymers) or hand dipped in a 3.0% (wt/vol) solution in methylene chloride (all Section B copolymers).
[2]This test measures the ability of a suture to be snugged-in. A loop is passed around a steel rod and tied with a square knot. The knot is set to a prescribed tension with an Instron tester, and the tension is then removed. After resetting the gage length and removing the steel rod, the loop is tested to break. The force and crosshead movement are recorded by an attached computer which calculates the work needed to move the crosshead 15 mm. Samples are tested immediately after 30 seconds immersion in saline solution (0.9% NaCl in distilled water). The number of specimens used in this test was 5, except for the uncoated braid, which used 3 specimens. The tensions used to set the knots, and all the other conditions of knot tying and testing, are practical laboratory conditions, but may

TABLE II-continued not correspond to actual surgical practice. The knot snug-in may not correlate with clinical experience.
[3] A strand is tied to itself to form a loop using a square + 1 knot. The second and third throws of the knot are set to a prescribed tension, the loop is cut, and the cut ends are clamped in the jaws of an Instron tester. In the same way as was described above for snug-in, the work required to move the crosshead 10 mm is determined. Samples are tested immediately after 30 seconds immersion in saline solution. The number of specimens used in the test was 10.
[4] Square knots were formed in hand-dipped (Section B) or machine coated (Section A) 1/0 polyglycolic acid braid using a conventional suture tying board. The knot was then run down to the board to assess the stick-slipping of the knot (chatter) as it runs down and to assess the force required to initiate and sustain the run-down. The abbreviations are: R, Runs; L, Lock; RC, Runs with Chatter; RD, Runs with Difficulty; RU, Runs with Unpredictability; RW, Runs Well. The comparisons are made on suture wet with saline.

TABLE III

In Vivo Coating Evaluations[1]

| Coating Polymer From: | Wt. %[2] Coating | Knot Repositioning[3] Ability | Knot Security[4] Category: A | B |
|---|---|---|---|---|
| Uncoated Braid | 0 | 0/8 | 4/4 | 0/4 |
| Example 1 | 0.94 | 4/5 | 5/5 | 0/5 |
|  | 1.54 | 4/5 | 5/5 | 0/5 |
|  | 2.57 | 5/5 | 5/5 | 0/5 |
| Example 2 | 1.39 | 10/10 | 9/10 | 1/10 |
|  | 2.24 | 10/10 | 9/10 | 1/10 |
| Example 3 | 1.37 | 10/10 | 10/10 | 0/10 |
|  | 2.04 | 10/10 | 7/10 | 3/10 |
| Example 4 | 1.77 | 10/10 | 10/10 | 0/10 |
|  | 1.91 | 10/10 | 10/10 | 0/10 |
| Example 6 | 1.34 | 10/10 | 10/10 | 0/10 |
|  | 1.93 | 10/10 | 9/10 | 1/10 |

TABLE III FOOTNOTES

[1] Coated, needled and sterilized sutures were tested in dogs.
[2] The coatings were applied to 1/0 polyglycolic acid braid from a 3.5% (wt/vol) solution of the coating material dissolved in acetone using a capillary coating machine.
[3] A suture coated with the test material is passed through two sides of a wound in the animal. A square knot is formed in the suture approximately 12-15 mm from the final knot position required to close the wound. The two ends of the suture are then pulled to slide the knot into position. Knots that slide properly are rated 1 while knots that fail to move into position are rated 0. The rating for a coating is the sum of the "1" ratings divided by the total number of test specimens.
[4] Immediate knot security is determined by using a pair of curved tweezers to tug at the 8 to 10 mm length of the ears of a square knot with two additional throws. Knots that are secure when manipulated are rated 1, knots with a loose top throw are rated 2, knots with an open top throw are rated 3, and knots that are not secure when manipulated are rated 4. The number of knots falling into each category is then divided by the total number of test specimens to provide a rating in each category. Samples rated 1 or 2 are designated A in the table, those rated 3 or 4 are designated B.

EXAMPLE 19

Synthesis of ε-Caprolactone-1-Lactide AB Block Copolymer

ε-Caprolactone (55 g, 0.482 mole), lauryl alcohol (0.148 g, 7.32×10$^{-4}$ mole) and stannous chloride dihydrate (7.19 mg, 3.19×10$^{-5}$ mole) were combined in a stirred reactor at 154° C. The mixture was stirred for 2 hours at 162° C. to 172° C. 1-Lactide (83 g, 0.58 mole) was added and the temperature was gradually increased to 220° C. The mixture was stirred for 1 hour. More 1-lactide (77 g, 0.53 mole) was added. The mixture was stirred for 1 hour. The resulting copolymer ηinh was 1.15 dl/g (0.5 g/dl in HFAS). The composition, as measured by $^1$H NMR was 27 wt. % caprolactone and 73 wt. % lactide.

EXAMPLE 20

Synthesis of ε-Caprolactone-1-Lactide AB Block Copolymer

ε-Caprolactone (112 g, 0.98 mole), lauryl alcohol (0.193 g, 8.5×10$^{-4}$ mole) and stannous chloride dihydrate (19.15 mg, 8.5×10$^{-5}$ mole) were combined in a stirred reactor at 162° C. The mixture was stirred at 162° C. for 6 hours. The temperature was increased to 180° C. and 16 g of 1-lactide was added (0.11 mole). The temperature was gradually increased to 220° C. over 1 hour and then 84 g 1-lactide was added. The mixture was stirred for 45 min. The resulting polymer had an inherent viscosity of 1.26 dl/g (0.5 g/dl in HFAS). The composition was determined by $^1$H NMR to be 53 wt. % caprolactone and 47 wt. % lactide.

EXAMPLE 21

Synthesis of ε-Caprolactone-1-Lactide ABA Block Copolymer

ε-Caprolactone (55 g, 0.482 mole), diethylene glycol (0.201 g, 1.90×10$^{-3}$ mole) and stannous chloride dihydrate (7.19 mg, 3.19×10$^{-5}$ mole) were combined in a stirred reactor at 154° C. The mixture was stirred for 2 hours at 162° C. to 172° C. 1-Lactide (20 g, 0.14 mole) and stannous chloride dihydrate (7.19 mg, 3.19×10$^{-5}$ mole) were added and the temperature was gradually increased to 200° C. The mixture was stirred for 0.5 hours. More 1-lactide (140 g, 0.97 mole) was added. The mixture was stirred for 1 hour. The resulting copolymer ηinh was 1.29 dl/g (0.5 g/dl in HFAS). The composition, as measured by $^1$H NMR, was 26 wt. % caprolactone and 74 wt. % lactide.

Table IV summarizes the in vitro performance for the bioabsorbable coatings of this invention.

TABLE IV

IN VITRO COATING PERFORMANCE

| Coating Polymer From: | # Dips[1] | Hand Tested Wet Knot Run Down[2] |
|---|---|---|
| Example 19 | 1 | L |
| Example 20 | 1 | RD |
| Example 21 | 1 | L |

TABLE IV FOOTNOTES

[1] The coatings were applied to 1/0 polyglycolic acid braid by hand dipping in a 2% (wt/vol.) solution of the coating material dissolved in methylene chloride.
[2] Square knots were formed in hand-dipped 1/0 polyglycolic acid braid using a conventional suture tying board. The knot was then run down to the board to assess the stick-slipping of the knot (chatter) as it runs down and to assess the force required to initiate and sustain the run-down. The abbreviations are: R, Runs; L, Locks; RC, Runs with Chatter; RD, Runs with Difficulty; RU, Runs with Unpredictability; RW, Runs Well. The comparisons are made on suture wet with saline.

We claim:

1. A surgical article having improved knot repositioning characteristics, the article comprising a multifilamentary strand, the strand having a bioabsorbable coating, the coating comprising a block copolymer having one or more A blocks solely manufactured from the monomer caprolactone, and one or more B blocks manufactured from the monomer caprolactone randomly copolymerized with one or more monomers selected from the group consisting of lactides, carbonates and a lactone other than caprolactone, the total caprolactone linkages in the copolymer being more than 50 to about 80 percent by weight of said copolymer.

2. An article of claim 1 wherein the caprolactone is ε-caprolactone.

3. An article of claim 1 wherein the caprolactone in the one or more A blocks is up to 70 percent by weight of the copolymer.

4. An article of claim 3 wherein the caprolactone in the one or more A blocks is about 40 percent by weight of the copolymer.

5. An article of claim 1 wherein the one or more B blocks are manufactured from caprolactone and glycolide.

6. An article of claim 5 wherein the glycolide in the one or more B blocks comprises up to 50 percent by weight of the copolymer.

7. An article of claim 5 wherein the glycolide in the one or more B blocks comprises up to about 65 percent by weight of said B blocks.

8. An article of claim 1 wherein the inherent viscosity of the copolymer is about 0.1 to 1.0 dl/g (0.5 g/dl in CHCl$_3$, 30° C.).

9. An article of claim 7 wherein the inherent viscosity of the copolymer is about 0.4 to 0.8 dl/g (0.5 g/dl in CHCl$_3$, 30° C.).

10. An article of claim 1 wherein the surgical article is bioabsorbable.

11. An article of claim 10 wherein the bioabsorbable surgical article is a suture or ligature.

12. An article of claim 11 wherein the suture or ligature is manufactured from a polymer prepared from one or more monomers selected from the group consisting of lactides, carbonates and lactones.

13. An article of claim 12 wherein the suture or ligature is manufactured from a homopolymer prepared from the monomer glycolide.

14. An article of claim 12 wherein the suture or ligature is manufactured from a polymer prepared from at least the monomer lactide.

15. An article of claim 12 wherein the suture or ligature is manufactured from a copolymer prepared from the monomers glycolide and 1,3-dioxan-2-one.

16. An article of claim 14 wherein the suture or ligature is manufactured from a copolymer prepared from the monomers glycolide and lactide.

17. An article of claim 12 or 14 wherein the coating comprises about 1/10 to 5% by weight of the coated suture or ligature.

18. An article of claim 17 wherein the coating comprises about ¼ to 3% by weight of the coated suture or ligature.

19. A surgical suture or ligature having improved knot repositioning characteristics, comprising a bioabsorbable, multifilamentary strand manufactured from a polymer prepared from one or more monomers selected from the group consisting of glycolide, lactide, 1,3-dioxan-2-one and 1,4-dioxane-2-one, the strand having a bioabsorbable coating, the coating comprising a block copolymer having one or more A blocks comprising caprolactone, wherein the caprolactone in the one or more A blocks is about 40 percent by weight of the copolymer, and one or more B blocks manufactured from the monomer caprolactone randomly polymerized with one or more monomers selected from the group consisting of lactides, the total caprolactone linkages in the copolymer being about 70 percent by weight of said copolymer, wherein the coating comprises about 1/10 to 5 percent by weight of the coated suture or ligature.

20. A suture or ligature of claim 19 wherein the one or more B blocks are manufactured from caprolactone and glycolide.

21. A suture or ligature of claim 20 wherein the inherent viscosity of the copolymer is about 0.4 to 0.8 dl/g (0.5 g/gl in CHCl$_3$, 30° C.).

22. A suture or ligature of claim 21 wherein the coating comprises about ¼ to 3% by weight of the coated suture or ligature.

23. A surgical suture or ligature having improved knot repositioning characteristics, comprising a bioabsorbable, multifilamentary strand manufactured from a polymer prepared from one or more monomers selected from the group consisting of glycolide, lactide, 1,3-dioxan-2-one and 1,4-dioxan-2-one, the strand having a bioabsorbable coating, the coating comprising a block copolymer having one or more A blocks comprising caprolactone, wherein the caprolactone in the one or more A blocks is about 40 percent by weight of the copolymer, and one or more B blocks manufactured from one or more monomers selected from the group consisting of lactides, carbonates and a lactone other than caprolactone, the total carprolactone linkages in the copolymer being about 70 percent by weight of said polymer, wherein the coating comprises about 1/10 to 5 percent by weight of the coated suture or ligature.

24. A suture or ligature of claim 23 wherein the one or more B blocks are manufactured from glycolide and 1,3-dioxan-2-one.

25. A suture or ligature of claim 24 wherein the inherent viscosity of the copolymer is about 0.1 to 04. dl/g (0.5 g/gl in CHCl$_3$, 30° C.).

26. A suture or ligature of claim 25 wherein the coating comprises about ¼ to 3% by weight of the coated suture or ligature.

* * * * *